United States Patent [19]
Uchida et al.

[11] Patent Number: 6,128,091
[45] Date of Patent: Oct. 3, 2000

[54] ELEMENT AND APPARATUS FOR ATTENUATED TOTAL REFLECTION MEASUREMENT, AND METHOD FOR MEASURING SPECIFIC COMPONENT USING THE SAME

[75] Inventors: Shinji Uchida, Neyagawa; Hiroshi Atsuta, Katano, both of Japan

[73] Assignee: Matsushita Electric Industrial Co., Ltd., Osaka, Japan

[21] Appl. No.: 09/139,652

[22] Filed: Aug. 25, 1998

[30] Foreign Application Priority Data

Aug. 26, 1997 [JP] Japan ..................................... 9-229816

[51] Int. Cl.[7] ........................... G01N 21/01; G01N 21/17
[52] U.S. Cl. ...................... 356/432; 356/300; 250/339.11
[58] Field of Search ........................ 250/339.07, 339.11; 356/300, 432

[56] References Cited

U.S. PATENT DOCUMENTS

| | | | |
|---|---|---|---|
| 5,172,182 | 12/1992 | Sting et al. | 356/300 |
| 5,229,611 | 7/1993 | Ukon | 250/339.07 |
| 5,729,018 | 3/1998 | Wells et al. | 250/339.07 |

FOREIGN PATENT DOCUMENTS

| | | |
|---|---|---|
| 0 304 092 | 2/1989 | Germany . |
| 38 30 002 | 3/1990 | Germany . |
| 0 478 137 | 4/1992 | Germany . |
| 42 27 813 | 2/1994 | Germany . |
| 44 25 445 | 1/1996 | Germany . |
| 7-184883 | 7/1995 | Japan . |
| 09113439 | 2/1997 | Japan . |
| 9-113439 | 5/1997 | Japan . |

OTHER PUBLICATIONS

H. Fukushima, et al.,; "Non–Invasive Measuring Method of Blood Sugar Value—Development of Optical Glucose Sensor—"; BME, vol. 4, No. 8 (Institute of Japan Medical Electronics, 1991).

"Electronically conductive Laser Waveguide for 'In Situ' Spectroscopic Study of the Interface Region and Surface of a Rotating Electrode", IBM Technical Disclosure Bulletin, Vol. 28, No. 12, 1986, pp. 5250–5252.

*Primary Examiner*—F. L. Evans
*Attorney, Agent, or Firm*—McDermott, Will & Emery

[57] ABSTRACT

An improved attenuated total reflection (ATR) element and the measurement apparatus employing the element capable of performing a measurement with a high accuracy at a low operating cost is disclosed. An ATR element of the present invention permits an incident beam to have an internal total reflection at the surface, and comprises a projection protruded at the portion where the incident beam has the internal total reflection.

15 Claims, 6 Drawing Sheets

ELEMENT AND APPARATUS FOR ATTENUATED TOTAL REFLECTION MEASUREMENT, AND METHOD FOR MEASURING SPECIFIC COMPONENT USING THE SAME

BACKGROUND OF THE INVENTION

The present invention relates to a measurement of a specific component in a subject, for instance, blood sugar level of human or animal, by utilizing an attenuated total reflection (hereinafter referred to as "ATR").

Hitherto, various methods for detecting and determining a specific component in a living body, by using the ATR measurement apparatus have been proposed.

For instance, in Japanese Unexamined Patent Publication Hei 9-113439, there is proposed a method for measuring the blood sugar level by permitting a transparent ATR prism 50 having a pair of reflecting surfaces, which are parallelly confronting each other, to be in close contact with top and bottom lips as shown in FIG. 8. According to this method, while the ATR prism 50 is held in the mouth and pressed against the top and bottom lips, an incident beam is permitted to enter the ATR prism 50 and to repeat attenuated total reflections at the border between the reflecting surfaces of the ATR prism 50 and the lips, as designated by the broken line. The beam propagated through the ATR prism 50 is finally issued from the ATR prism 50. Information on specific substances in the lips can be obtained by analyzing the issued beam.

There is proposed another method in BME, Vol. 5, No. 8 (Institute of Japan Medical Electronics, 1991). This publication proposes a method for measuring the blood sugar level or blood alcohol level in which an ATR prism made of an optical crystal of ZnSe or the like is closely adhered to a mucus membrane of lips, then a laser beam with a wavelength of 9 to 11 $\mu$m is permitted to enter the ATR prism and to have multiply internal total reflection inside the ATR prism. In this method, an absorbed light or the scattered and reflected light is analyzed. According to this method, a realtime measurement of the blood sugar level or blood alcohol level can be made in a non-invading manner.

These methods utilize an evanescent wave (so called "oozing light") for a quantitative analysis. That is, when a surface of the ATR prism 50 is pressed against a subject, a beam traveling through the ATR prism 50 totally reflects after slightly invading the lips at the surface as shown in FIG. 8. When the ATR prism 50 is sandwiched by lips, the beam invades the lips and is therefore affected by the respective components in a blood circulating through the lips. In this manner, by measuring an intensity of the reflected beam, it is possible to detect the change in the light transmittance, reflectance, absorbance, or the like of the blood, and thus the information concerning the respective components in the blood can be obtained.

However, the above-mentioned conventional ATR measurement apparatuses have the following problems.

It is hard to obtain the information on the deep spots of the living body, because the depth of the evanescent wave invasion is in an order of wavelength and the reflected beam contains a large amount of light which transmits through the spot near the surface. In particular, if any impurity exists on the border between the prism and the subject, the obtained signal is deteriorated.

Therefore, in the case of pressing the ATR prism against the lips as in the above-mentioned conventional examples, the adhesion between the surface of the ATR prism and the lips is not stable and thus it is difficult to conduct a measurement with a high accuracy. In addition, in a case where the saliva invades between the ATR prism and the lips, the measurement values are greatly affected by the saliva.

Further, an optical crystal of ZnSe, ZnS or the like which has widely been used as the conventional ATR prism for the above-mentioned measurement apparatuses has a very expensive price. In addition, it is difficult to apply such ATR prism to continuous measurements for a number of the subjects because the ATR prisms are very soft and require great care for their handling and washing.

BRIEF SUMMARY OF THE INVENTION

The object of the present invention is to solve the above-mentioned problems and to provide an attenuated total reflection (ATR) element and the measurement apparatus which can conduct the measurement with a high accuracy and a low operating cost.

The present invention provides an ATR element which permits an incident beam to enter therein and to have an internal total reflection at the surface. The ATR element comprises a projection protruded at the portion where the incident beam has the internal total reflection.

In a preferred mode of the present invention, the ATR element is made of a single crystal of silicon.

In another preferred mode of the present invention, the projection has a pedestal or triangular cross-sectional profile. It is preferable that the ATR element is formed by anisotropically etching a single crystal of silicon.

In still another preferred mode of the present invention, the projection is provided on one of two confronting surfaces, and the beam is made incident upon and issued from the other.

It is preferable that the ATR element has a lens for collecting and radiating the incident beam towards the projection on the surface on which the beam is made incident.

In still further preferred mode of the present invention, the surface on which the projection is provided is curved.

The present invention also provides an ATR measurement apparatus comprising:

a light source;

a transparent ATR element which permits a beam projected by the light source to enter therein and to have an internal total reflection at the surface; and a light detector which detects the beam issued from the ATR element, wherein the ATR element has a projection protruded at the portion where the beam has the internal total reflection.

By employing the ATR element in combination with a light source for projecting a beam to the ATR element, and a light detector which detects the beam issued from the ATR element, an excellent ATR measurement apparatus can be obtained.

The present invention further provides a method for measuring a specific component comprising the steps of:

permitting a transparent ATR element having projections to be in contact with a subject;

projecting a beam to the transparent ATR element so as to enter therein and to have an internal total reflection at the projections; and detecting the beam issued from the ATR element after the internal total reflection.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

In the following paragraphs, preferred embodiments of the present invention will be described in more detail with reference to the attached drawings.

EXAMPLE 1

Figure 1A:
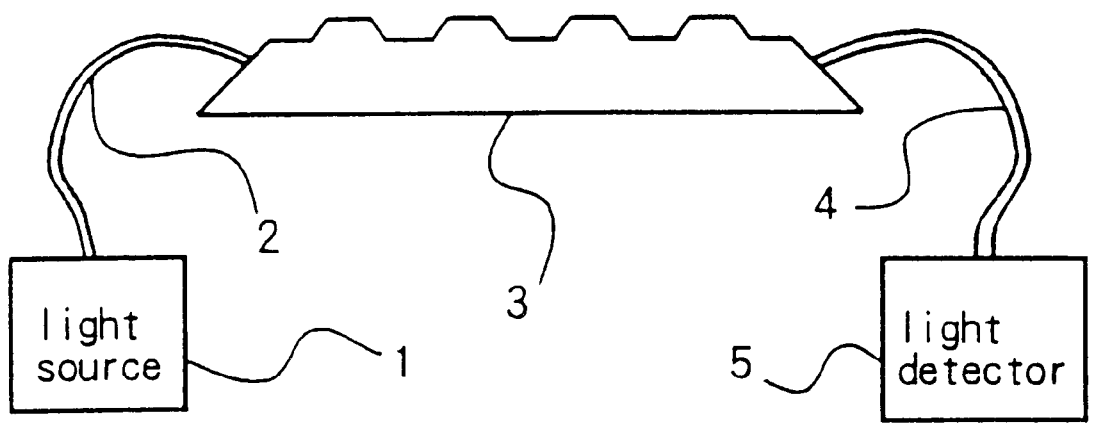
FIG. 1A shows an outline of an attenuated total reflection measurement apparatus in one example of the present invention.
Figure 1B:
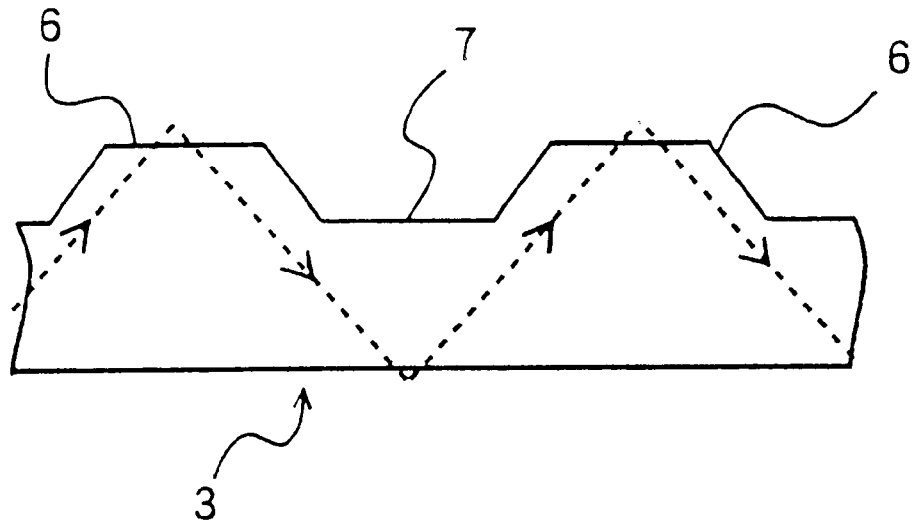
FIG. 1B shows a mode of propagation of a beam through an ATR element of the ATR measurement apparatus.

FIG. 1 shows an outline of the ATR measurement apparatus of the present example.

As a light source 1, a high brightness ceramic light source which emits a beam with a wavelength of 1.3 to 10 $\mu$m is used, for instance. An optical fiber 2 transmits the beam emitted by the light source 1 and permits the beam to be made incident upon an ATR element 3. The beam incident upon the ATR element 3 enters inside and repeats total reflections at the top and bottom surfaces of the ATR element 3, alternately. Then, the beam is issued outside as shown by the broken line in the figure. The beam issued outside of the ATR element 3 reaches a light detector 5 through an optical fiber 4. The light detector 5 analyzes a spectrum or the like of this beam and displays the result of the analysis on a display device (not shown).

On the top surface of the ATR element 3, a plurality of projections 6 protruded in a trapezoidal profile are so arranged that the beam incident upon the ATR element 3 has total reflections at the top surfaces of the projections 6. The height of the projections 6 is preferably not less than 1 $\mu$m when a working precision is considered. It is preferably not more than 200 $\mu$m, when a close contact with the skin of a living body is considered.

The attenuated total reflection measurement apparatus of this example is suited for the measurement on a spectrometric characteristic of the blood flowing through blood vessels, by pressing the ATR element on a portion of the living body, in particular, on the lips where the skin is thinner than that on other portions.

By providing the projections on the spots of the ATR element which are in contact with the living body as described above, it is possible to allow the ATR element to have close contacts with the living body at the plurality of the projections in a stable manner.

Further, the surface of the ATR element or the projections can penetrate inside the living body as compared with the surface of the conventional flat ATR prism.

For that reason, it is possible to allow the evanescent wave to enter the living body more deeply by permitting the beam incident upon the ATR element to have internal reflections at the top surfaces of the projections.

Therefore, by employing this ATR element, a signal with a higher sensitivity can be obtained in a stable manner. Further, if the surface of the ATR element for the contact with the living body is configured to be a lens-like curved surface and the above-mentioned projections are provided thereon, a more stable close contact can be obtained when the ATR element is held between the top and bottom lips.

The information obtained by the conventional ATR prism contains an influence of the saliva or the like if it exists between the prism and the lips. On the contrary, the ATR element of this example can suppress such influence by providing the plurality of the projections 6 on the surface for being pressed against the lips, even if the saliva or the like exists thereon. This is because, it is collected in the troughs 7 between the projections 6 which have no relationship with the total reflection.

In the ATR measurement apparatus of this example, a single crystal of Si having a high refractive index is used as the material for the ATR element. ZnSe is conventionally used as the material for the ATR prism, but it is soft and liable to be damaged by scratching or other hazard. For that reason, in the practical use, the closest attention should be paid in order to prevent such damage.

In contrast, silicon has only a small apprehension for such damage. Further, since it is widely used as the material for the semiconductor devices, it costs very low. Therefore, the ATR element of silicon has a small economical charge even if it is not repetitively used as in the case of using the ATR element of expensive ZnSe. Further, even in the repetitive use, washing, disinfection or other handling of the element is very easy.

EXAMPLE 2

Figure 2:
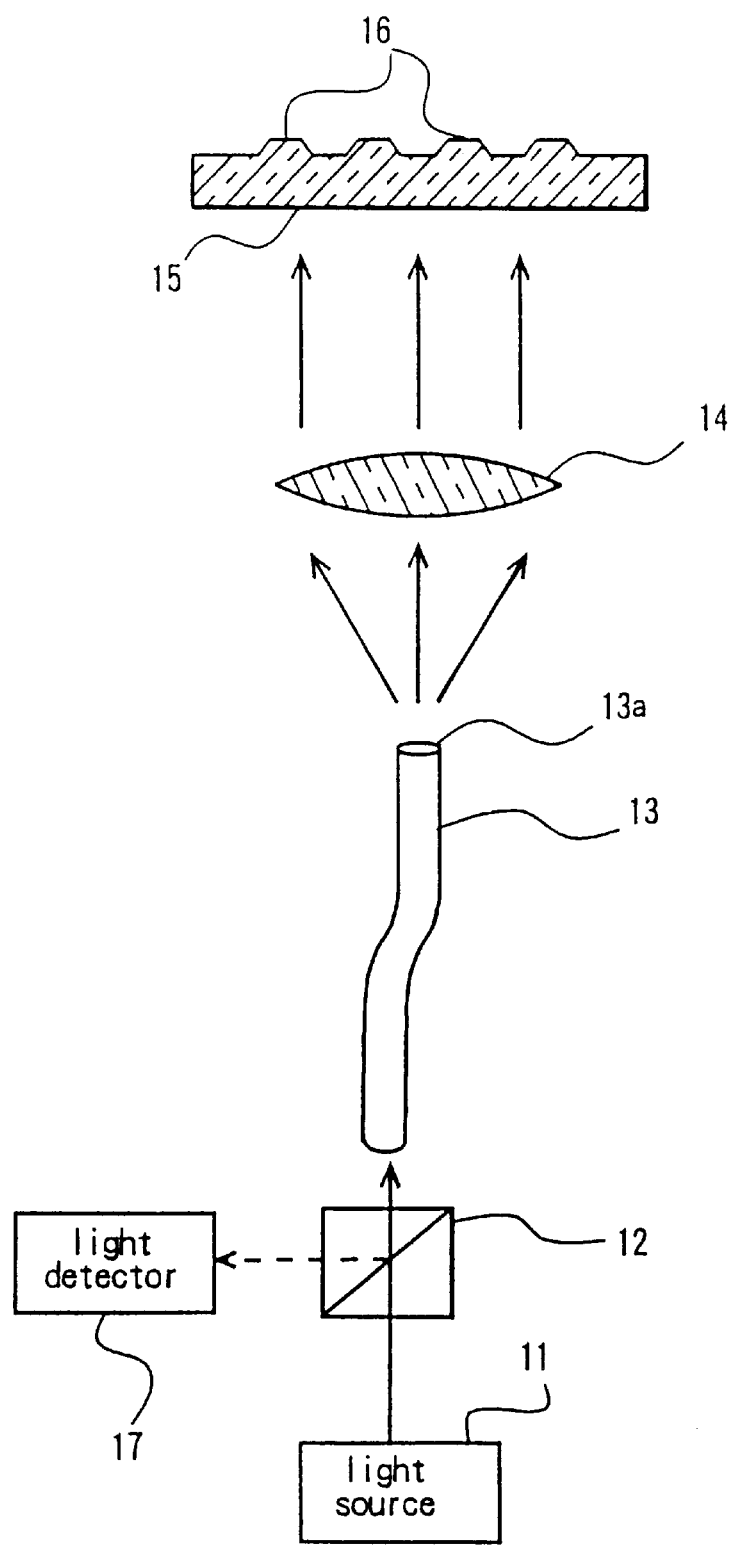
FIG. 2 shows an outline of a configuration of an ATR measurement apparatus in another example of the present invention.

An outline of the ATR measurement apparatus in this example is shown in FIG. 2.

A beam projected from a light source 11 passes through a beam splitter 12, then reaches an optical fiber 13. The beam reached the optical fiber 13 transmits therethrough and is issued from an emitting end 13a of the optical fiber 13. The beam issued from the emitting end 13a radiates but is converted into a parallel beam by a collimator lens 14, and then projected upon a plate-shaped ATR element 15 made of Si single crystal along the normal direction.

Figure 3A:
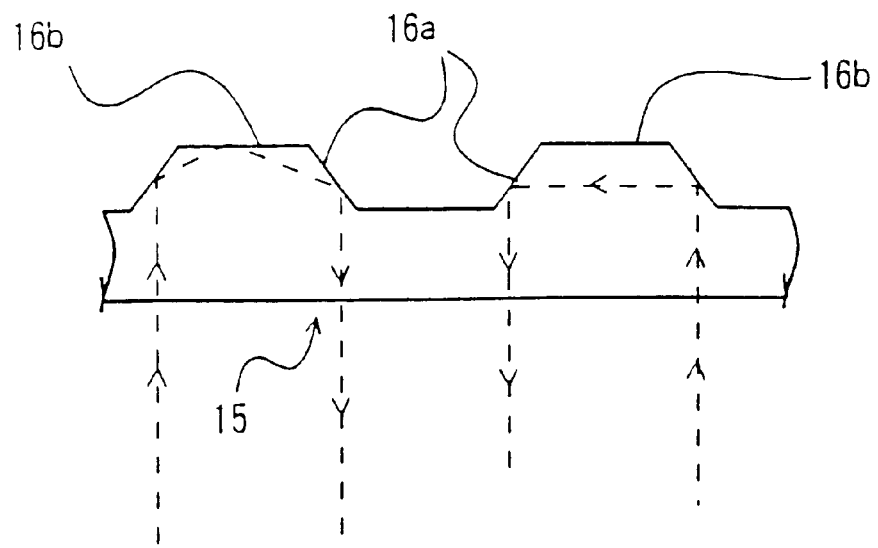
FIG. 3A is a schematic view of the ATR element showing locus of the beam propagating therethrough at the measurement.
Figure 3B:
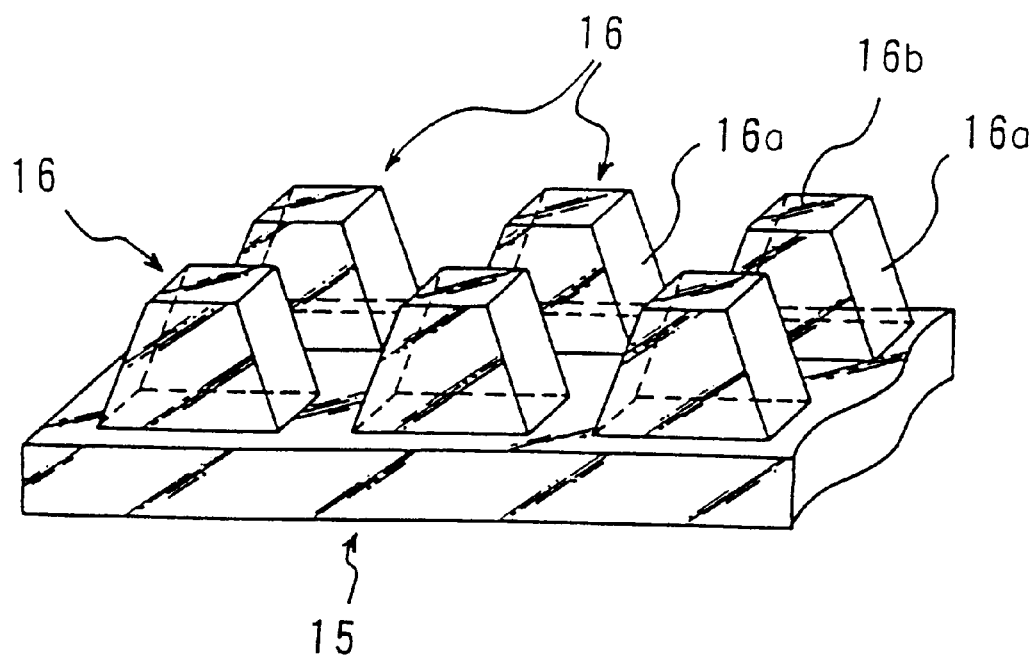
FIG. 3B shows a perspective view of the ATR element.

On a surface of the ATR element which is opposite to the surface of light incidence, a plurality of projections 16 are provided as shown in FIG. 3. The beam entering the ATR element 15 reflects at one of inclined side faces 16a, a top face 16*b* and the other of side faces 16*a* in this order. Then the beam is issued from the surface of incidence. The beam issued from the ATR element 15 passes through the collimator lens 14 and the optical fiber 13. Then the beam reaches a light detector 17 after reflecting on the beam splitter 12.

The ATR measurement apparatus of this example is suited for conducting an analysis on the respective components in the blood of the living body, by pressing the surface provided with the projections 16, i.e., the surface which is opposite to the surface of light incidence, of the ATR element 15 on, for instance, the skin of the living body.

In particular, by providing the projections of trapezoidal profiles having a inclined side faces on the ATR element, it is possible to allow the measuring surface to have close contact with the living body in a stable manner. Further, since the projections are able to encroach upon the tissue of the living body, it is possible to obtain the information on the deeper part of the living body.

Moreover, since the ATR measurement apparatus can permit the beam to be issued from the incident surface of the ATR element 15, there is no need for holding the ATR element 15 between the top and bottom lips as required in the conventional example and Example 1. By employing the ATR measurement apparatus of this example, it is possible to conduct the measurement only by pressing the measuring surface of the ATR element on the skin.

Figure 4:
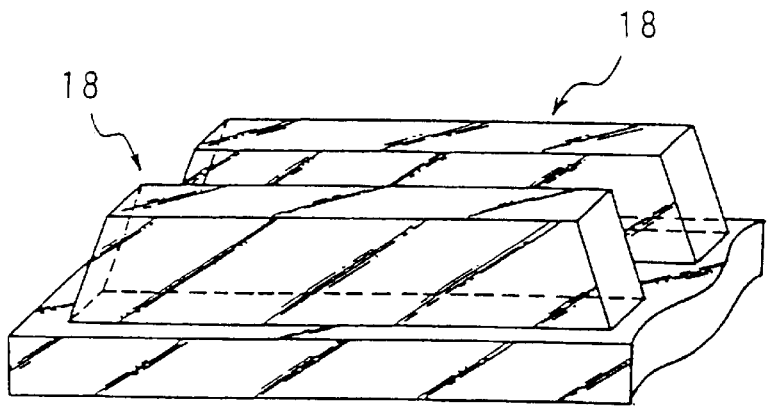
FIG. 4 shows a perspective view of another ATR element for the ATR measurement apparatus.

In the above-mentioned example, the plurality of the projections having a trapezoidal cross-sectional profile are arranged on the measuring surface of the ATR element around the front/rear and the left/right parts thereof. However, the cross-sectional profile of the projections may be another shape such as a triangular shape. Further, as shown in FIG. 4, a plurality of the projections 18 each having a trapezoidal cross-sectional profile and a continued apex may be provided.

It is preferable to process the ATR element to have a lens-like curved outer shape and to provide the above-mentioned projections thereon. In this case, even if the ATR element is forcefully pressed onto the living body, it gives only a small pain to the living body.

In the case of the ATR element made of single crystal silicon, the projections are provided by subjecting a crystal silicon substrate to anisotropical etching. This method is a chemical etching using an aqueous solution of KOH or an aqueous solution of ethylene diamine, by utilizing the fact that an etching rate of the single crystal silicon along the (111) direction is much smaller than those along the other directions.

Figure 5:
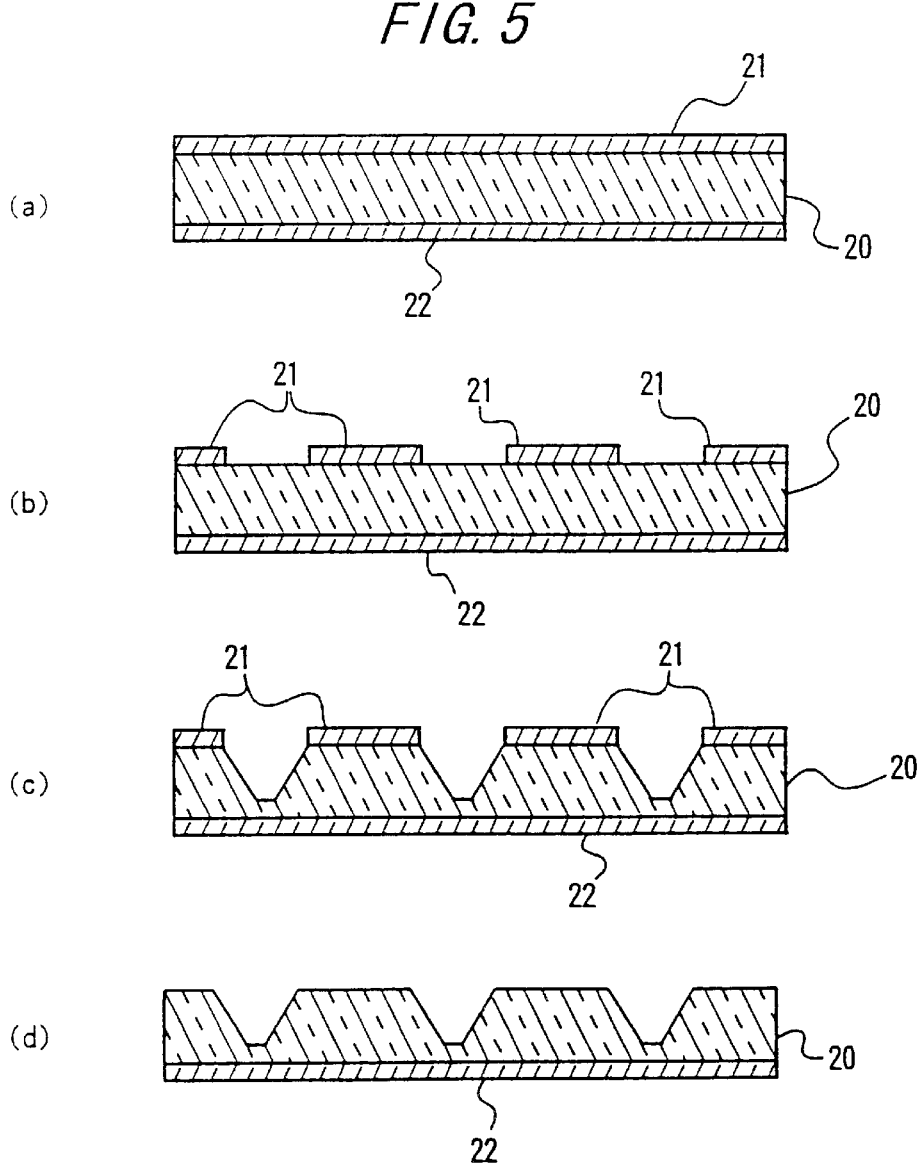
FIG. 5 shows states of a substrate for the ATR element in the respective steps of producing.

First, as shown in FIG. 5(*a*),the top and bottom surface of the single crystal silicon substrate 20 are coated with oxide films 21 and 22 as protective layers. Then, the oxide film 21 is processed to have a desired pattern as shown in FIG. 5(*b*). Subsequently, this silicon substrate 20 is etched by being immersed in, for instance, a 40% KOH aqueous solution. When a silicon wafer whose (100) crystal face is oriented along the normal line of the surface, the projections 23 whose side face is inclined at 54.7 degree are formed as shown in FIG. 5(*c*). After the formation of the projections 23, the oxide film 21 and 22 are removed as shown in FIG. 5(*d*).

In the above procedure, a film consisting of a nitride of silicon may be used as the protective layer.

EXAMPLE 3

Figure 6:
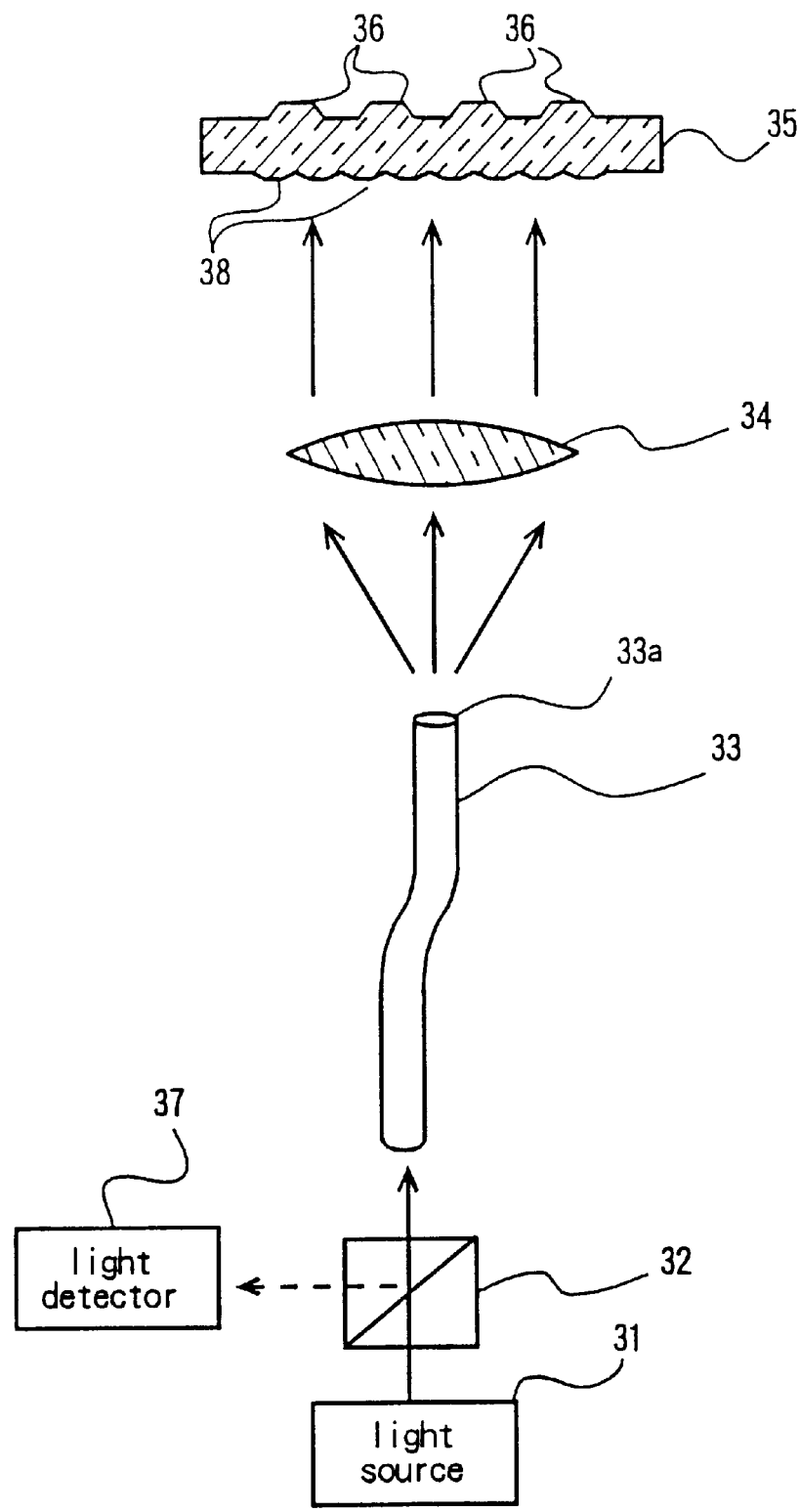
FIG. 6 shows an outline of a configuration of an ATR measurement apparatus in still another example of the present invention.
Figure 7A:
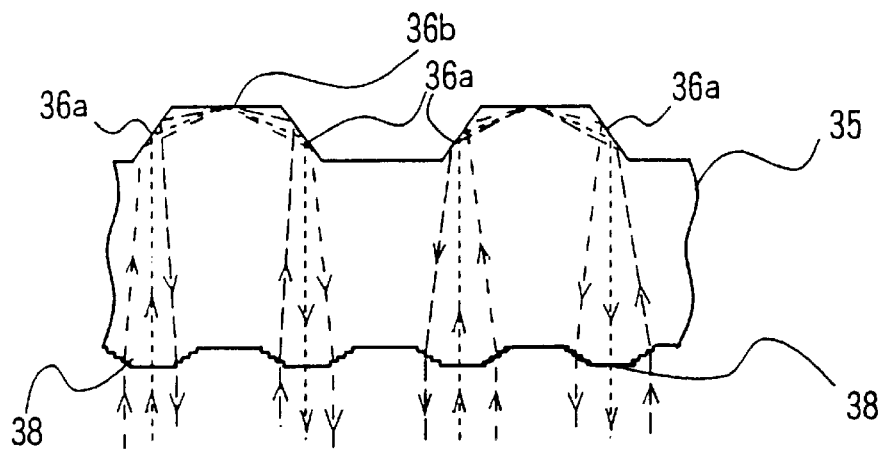
FIG. 7A is a schematic view of the ATR element showing locus of the beam propagating therethrough at the measurement.

FIG. 6 shows an outline of the ATR measurement apparatus of this example. A beam projected from a light source 31 passes through a beam splitter 32 and reaches an optical fiber 33 in a manner similar to that of Example 2. The beam reached an optical fiber 33 transmits therethrough and is issued from an emitting end 33*a*. The beam is then converted into a parallel beam by a collimator lens 34. The beam reached an ATR element 35 is refracted by a micro lens 38 formed on the incident surface of the ATR element 35, and is selectively projected onto an inclined side face 36*a* of projections 36 as shown in FIG. 7. Then, the beam totally reflects at the side face 36*a* and is collected at a top face 36*b*. After reflecting at the top face 36*b*, the beam totally reflects at another side face 36*a* and issued from the ATR element 35.

The beam issued from the ATR element 35 reaches a light detector 37 through the collimator lens 34, the optical fiber 33 and the beam splitter 32.

Here, the micro lenses 38 are so arranged that they coincide with the points on the side faces 36*a* of the projections 36. Further, by arranging them so as to focus the beam on the respective projections 36, it becomes possible to permit the beam to be made incident upon the ATR element to have total reflection inside the ATR element 35, thereby utilizing the beam for the measurement efficiently. That is, if the incident surface of the ATR element is flat as in Example 2, a part of the beam incident upon the ATR element transmits through the border between the ATR element and the subject without reflection.

In contrast, by arranging the micro lenses 38 on the incident surface of the ATR element 35 and by selectively projecting the beam onto the side face of the projection, it becomes possible to permit the beam to totally reflect efficiently. Further, by inclining the side face of the projection, it becomes possible to permit the beam to totally reflect three times at the surfaces of the projection. Therefore, a measurement with a high accuracy and efficiency can be conducted.

Figure 7B:
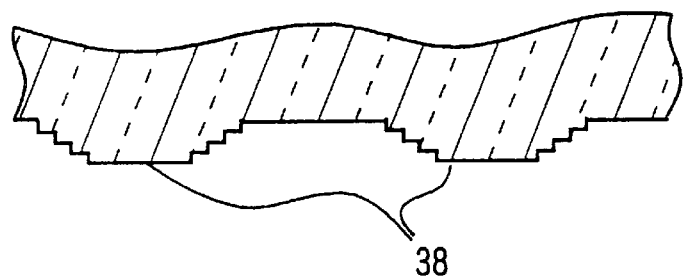
FIG. 7B shows a longitudinal cross-sectional view of an essential part of the ATR element.
Figure 8:
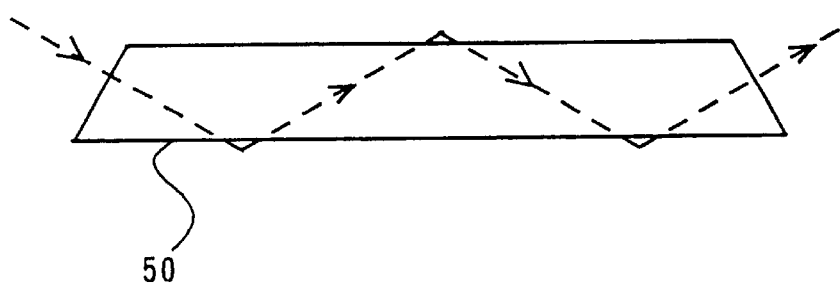
FIG. 8 shows an outline of an ATR measurement apparatus of the comparative example.

The micro lenses are formed by repeating, for instance photolithograph (optical curving or sculpturing) and etching, to have a step-like profile as shown in FIG. 7B.

Since the working technologies which have been established in the field of semiconductor can be applied to these, it is possible to work them with a good precision, at a low cost and in a large quantity. Therefore, it is possible to manufacture the ATR elements with high performance and a high quality at a low cost and in a large quantity.

In that case, the utilization rate of light can be further improved by forming a reflection-preventing film composed of diamond, DLC (diamond like carbon), ZnSe or the like on the surface of the micro lens.

In addition, a reflection-preventing effect can also be obtained by forming the surface of the micro lens to have unevenness in micron order.

As described above, according to the present invention, it becomes possible to provide an ATR element and the measurement apparatus capable of performing a measurement with high accuracy at a low operating cost.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

We claim:

1. An attenuated total reflection element which permits an incident beam to enter therein and to have an internal total reflection at the surface, comprising a projection protruded at the portion where said incident beam has said internal total reflection, and said projection having a height of 1 μm to 200 μm.

2. The attenuated total reflection element in accordance with claim 1, which is made of a single crystal of silicon.

3. The attenuated total reflection element in accordance with claim 1, wherein said projection has a trapezoidal or triangular cross-sectional profile.

4. The attenuated total reflection element in accordance with claim 3, which is formed by anisotropically etching a single crystal of silicon.

5. The attenuated total reflection element in accordance with claim 1, wherein said projection is provided on one of two confronting surfaces, and the beam is made incident upon and issued from the other.

6. The attenuated total reflection element in accordance with claim 5, further comprising a lens for collecting and projecting said incident beam towards said projection on the surface on which the beam is made incident.

7. The attenuated total reflection measurement element in accordance with claim 1, wherein the surface on which said projection is provided is curved.

8. An attenuated total reflection measurement apparatus comprising:
   a light source;
   a transparent attenuated total reflection element which permits a beam projected by said light source to enter therein and to have an internal total reflection at the surface; and
   a light detector which detects the beam issued from said attenuated total reflection element, wherein said attenuated total reflection element has a projection protruded at the portion where said beam has said internal total reflection, and said projection having a height of 1 μm to 200 μm.

9. The attenuated total reflection measurement apparatus in accordance with claim 8, wherein said projection has a trapezoidal or triangular cross-sectional profile.

10. The attenuated total reflection measurement apparatus in accordance with claim 8, wherein said attenuated total reflection element is made of a single crystal of silicon.

11. The attenuated total reflection measurement apparatus in accordance with claim 10, wherein said attenuated total reflection element is formed by anisotropically etching a single crystal of silicon.

12. The attenuated total reflection measurement apparatus in accordance with claim 8, wherein the surface of said attenuated total reflection element on which said projection is provided is curved.

13. The attenuated total reflection measurement apparatus in accordance with claim 8, wherein said projection is provided on one of two confronting surfaces, and the beam is made incident upon and issued from the other.

14. The attenuated total reflection measurement apparatus in accordance with claim 13, wherein said attenuated total reflection element comprises a lens on said surface on which said beam incidents, for collecting and projecting said beam towards said projection.

15. A method for measuring a specific component comprising the steps of:
   permitting a transparent attenuated total reflection element having projections to be in contact with a subject, said projecting having a height of 1 μm to 200 μm;
   projecting a beam to said transparent attenuated total reflection element so as to enter therein and to have an internal total reflection at said projections; and
   detecting the beam issued from said attenuated total reflection element after said internal total reflection.

* * * * *